United States Patent
Nonomura

(10) Patent No.: US 6,373,972 B1
(45) Date of Patent: Apr. 16, 2002

(54) MICROBE AND CELL FUNCTION CONTROL DEVICE, A MICROBIAL ECOLOGY DETECTOR DEVICE, AND A METHOD OF CONTROLLING A MICROBE AND CELL FUNCTION CONTROL DEVICE

(75) Inventor: Yuusuke Nonomura, Nagoya (JP)

(73) Assignee: Kabushiki Kaisha Marutomo, Aichi (JP)

( * ) Notice: Subject to any disclaimer, the term of this patent is extended or adjusted under 35 U.S.C. 154(b) by 0 days.

(21) Appl. No.: 08/993,713

(22) Filed: Dec. 18, 1997

(30) Foreign Application Priority Data

| Dec. 18, 1996 | (JP) | 8-354393 |
| Apr. 11, 1997 | (JP) | 9-110238 |
| Sep. 3, 1997 | (JP) | 9-255918 |
| Nov. 17, 1997 | (JP) | 9-333501 |
| Nov. 17, 1997 | (JP) | 9-333624 |
| Dec. 2, 1997 | (JP) | 9-332154 |
| Dec. 4, 1997 | (JP) | 9-334549 |

(51) Int. Cl.$^7$ ............................................. G06K 7/00
(52) U.S. Cl. ........................ 382/133; 382/128; 433/29; 348/66
(58) Field of Search ................. 433/215, 29, 229; 348/66; 606/10; 382/128, 100, 132; 600/473, 477, 476, 322; 378/38–39, 168–170, 189–191; 424/50; 514/54; 607/89; 426/238, 248; 250/228, 574, 341.8

(56) References Cited

U.S. PATENT DOCUMENTS

| 4,178,917 A | * 12/1979 | Shapiro | 600/322 |
| 4,438,093 A | * 3/1984 | Shimada et al. | 424/50 |
| 4,479,499 A | * 10/1984 | Alfano | 600/477 |
| 4,951,663 A | 8/1990 | L'Esperance, Jr. | 607/89 |
| 5,034,235 A | 7/1991 | Dunn et al. | 426/238 |
| 5,164,597 A | 11/1992 | Lodder | 250/341.8 |
| 5,306,144 A | * 4/1994 | Hibst et al. | 433/29 |
| 5,382,163 A | * 1/1995 | Putman | 433/215 |
| 5,622,939 A | * 4/1997 | Jamas et al. | 514/54 |
| 5,785,703 A | * 7/1998 | Goodman et al. | 606/10 |
| 5,894,620 A | * 4/1999 | Polaert et al. | 15/22.1 |
| 6,024,562 A | * 2/2000 | Hibst et al. | 433/29 |

FOREIGN PATENT DOCUMENTS

| DE | 39 03 777 | 8/1990 | C12Q/1/02 |
| EP | 0 500 387 | 8/1992 | A61K/37/50 |
| EP | 0 743 029 | 11/1996 | A46B/15/00 |

OTHER PUBLICATIONS

Harold R. Horn, "Porcelain Laminate Veneers Bonded to Etched Enamel," Dental Clinics of North America, vol. 27, No. 4, Oct. 1983, pp. 671–684.

* cited by examiner

Primary Examiner—Bhavesh Mehta
Assistant Examiner—Ishrat Sherali
(74) Attorney, Agent, or Firm—Gudrun E. Huckett

(57) ABSTRACT

In a microbe and cell function control device, a primary electromagnetic wave radiation member is provided to radiate electromagnetic wave on microbes and cells within a predetermined wave length range thereof. An electromagnetic wave measuring member measures an intensity of a predetermined range of the electromagnetic wave permeated or reflected from the microbes and cells. An absorption intensity distinction member determines wavelength the microbes and cells absorb based on the intensity of the electromagnetic wave measured by the electromagnetic wave measuring member. A secondary electromagnetic wave radiation member radiates the electromagnetic wave absorbed by the absorption intensity distinction member on the microbes and cells.

16 Claims, 7 Drawing Sheets

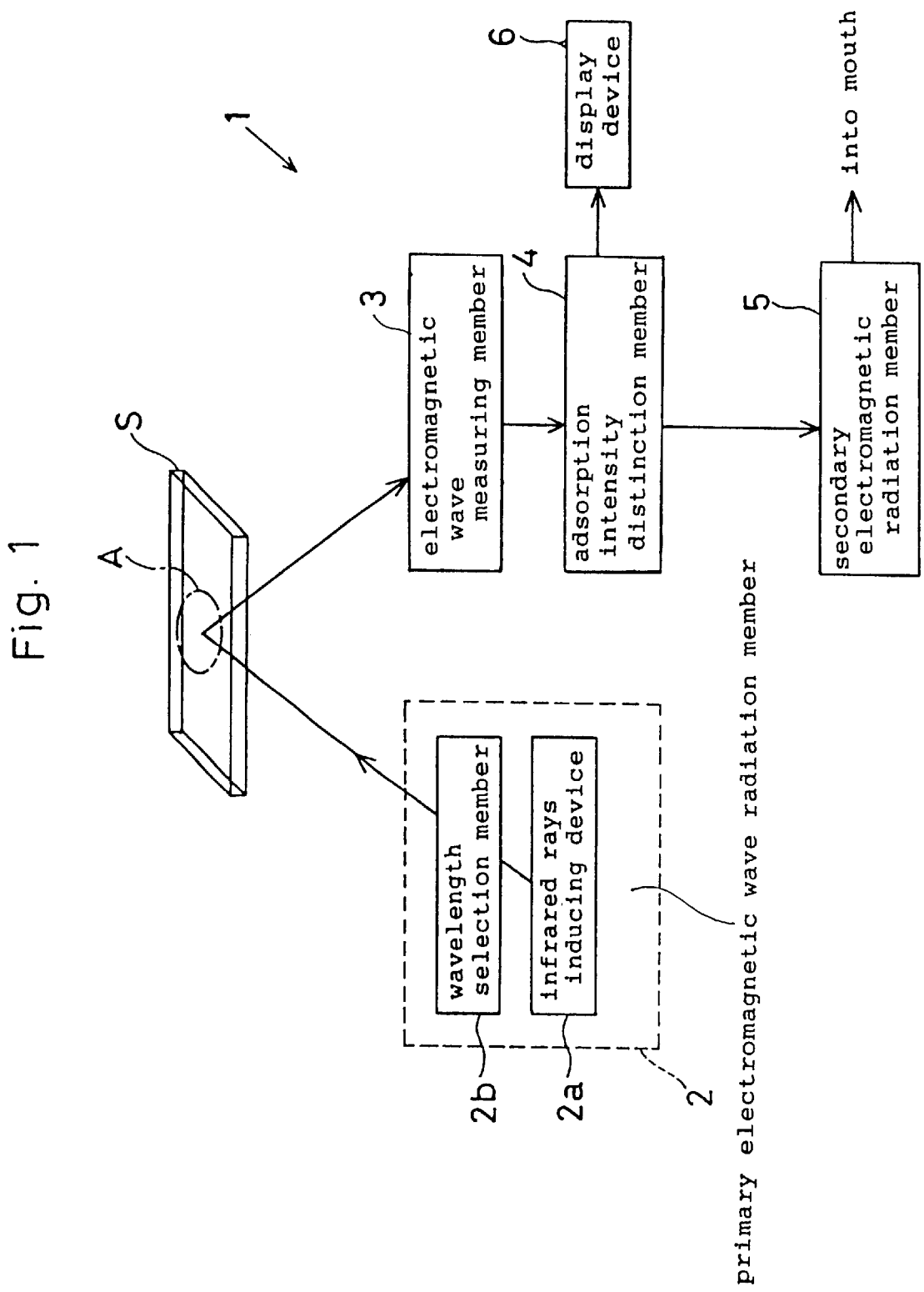

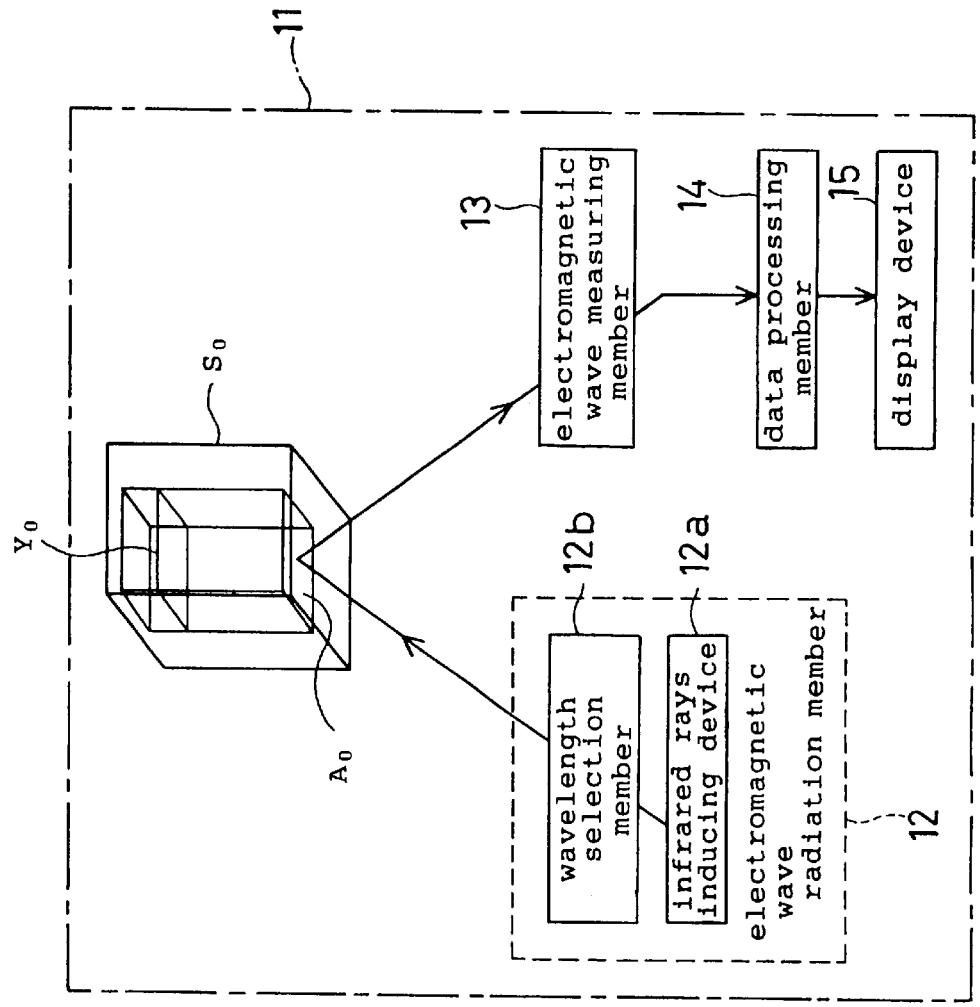

MICROBE AND CELL FUNCTION CONTROL DEVICE, A MICROBIAL ECOLOGY DETECTOR DEVICE, AND A METHOD OF CONTROLLING A MICROBE AND CELL FUNCTION CONTROL DEVICE

BACKGROUND OF THE INVENTION

1. Field of the Invention

The invention relates to a microbe and cell function control device which controls promotion and suppress of microbes (virus, leaven or the like) and cells taken or cultured from human, aminals, birds, fish, plants and the like). The invention further relates to a microbial ecology detector device which detects an amount of the microbes or cells and detects whether the microbes or cells are present or not, and particularly suited to detecting germs in plaque of human teeth.

2. Description of Prior Art

There has been hardly known about a control device which is capable of precisely controlling functional promotion and suppress of particular microbes and cells.

Take the germs in the mouth, for example, the device has been hardly introduced which is capable of detecting germs in human mouth to specify them presented in the mouth so as to suppress the functions of the germs, and avoid the decay of the teeth as preventive and diagnostic measures of pathogenic gingivitis. Even when the germs causing dental caries in the mouth is identified, there has been rarely so far presented a technique to suppress the microbial functions with the specified germs only as a target. With the use of the germicide agents, there is a possibility to sterilize other useful germs for hygienic purposese. When using the germicide agents strong enough to terminate all the germs in the mouth, it would adversely affects on the human health.

In the meanwhile, it has been introduced to breed a sample on agar so as to observe them after an elapse of a predetermined time period when detecting the presence or absence of the microbial ecology such as germs and cells.

A dental device has been desired to be introduced which enables to a stable detection when detecting the presence or absence of the microbial ecology. Because the individual observations often differ the resultant detection depending on the individual experience with much uncertainty to be left in the prior art visual observation.

Without a tool or device of detecting the germs in the dental plaque, it has been difficult to appropriately diagnose the individual patients in the dental clinic.

Therefore, it is an object of the invention to provide a microbe and cell function control device which is capable of precisely controlling function of particular microbes and cells.

It is another object of the invention to provide a microbial ecology detector device which is capable of detecting an amount of the microbes, cells or substances generated from the microbes or cells and detecting the presence or absence thereof.

SUMMARY OF THE INVENTION

According to one aspect of the invention, a primary electromagnetic wave radiation member radiates electromagnetic wave on microbes and cells within a predetermined wave length range thereof. An electromagnetic wave measuring member measures an intensity of a predetermined range of the electromagnetic wave permeated or reflected from the microbes and cells. An absorption intensity distinction member determines wavelength the microbes and cells absorb based on the intensity of the electromagnetic wave measured by the electromagnetic wave measuring member. A secondary electromagnetic wave radiation member radiates the electromagnetic wave absorbed by the absorption intensity distinction member toward the microbes and cells. As a result, it effectuates the functional suppression of the specified microbes and cells so as to control the functional promotion and suppression of the specified microbes.

According to another aspect of the invention, the electromagnetic wave radiation device radiates the electromagnetic wave absorbed by microbes and cells on said microbe and cells. This makes it possible to control the functional promotion and suppression of the specified microbes.

According to another aspect of the invention, a primary electromagnetic wave radiation member radiates electromagnetic wave on microbes and cells within a predetermined wave length ran thereof. An electromagnetic wave measuring member measures an intensity of a predetermined range of the electromagnetic wave permeated or reflected from the microbes and cells. An absorption intensity distinction member determines wavelength that the microbes and cells absorb based on the intensity of the electromagnetic wave measured by the electromagnetic wave measuring member. An electromagnetic wave absorption medium is administered to the microbes and cells so as to absorp the same wavelength of the electromagnetic wave determined by the absorption intensity distinction member. As a result, it effectuates the functional promotion and suppression of the specified microbes and cells so as to control the functional promotion and suppression of the specified microbes.

The electromagnetic wave absorption medium is to absorbe the predetermined wavelength of the electromagnetic wave. It is possible to reduce the toxicity of the wave absorption medium so as to neutralize the influence on human body.

According to another aspect of the invention, a primary electromagnetic wave radiation member radiates electromagnetic wave on microbes and cells within a predetermined wave length range thereof. An electromagnetic wave measuring member measures an intensity of a predetermined range of the electromagnetic wave permeated or reflected from the microbes and cell. An absorption intensity distinction member determines wavelength the microbes and cells absorb based on the intensity of the electromagnetic wave measured by the electromagnetic wave measuring member. An electromagnetic wave absorption medium preparation member prepares an electromagnetic wave absorption medium administered to the microbes and cells so as to absorp the same wavelength of the electromagnetic wave determined by the absorption intensity distinction member. As a result, it effectuates the functional promotion and suppression of the specified microbes and cells so as to control the functional promotion and suppression of the specified microbes.

The electromagnetic wave absorption medium is to absorbe the predetermined wavelength of the electromagnetic wave. It is possible to reduce the toxicity of the wave absorption medium so as to neutralize the influence on human health.

According to another aspect of the invention, an absorption medium preparation device prepares an electromagnetic wave absorption medium which absorps the same wavelength of the electromagnetic wave absorbed by the microbes and cells.

The electromagnetic wave absorption medium is to absorbe the predetermined wavelength of the electromagnetic wave, and it is possible to reduce the toxicity of the wave absorption medium compared to the prior art counterpart, so as to neutralize the influence on human health.

According to another aspect of the invention, when the electromagnetic wave absorption medium is administered to the specified microbes and cells, it effectuates the functional control of the microbes and cells.

It is to be noted that the electromagnetic wave absorption medium is to absorbe the predetermined wavelength of the electromagnetic wave. It is possible to reduce the toxicity of the wave absorption medium compared to the prior art counterpart, so as to neutralize the influence on human health.

According to another aspect of the invention, a primary electromagnetic wave is radiated toward micrcobes and cells within a predetermined wave length range thereof. An intensity of a predetermined range of the electromagnetic wave is measured which is permeated or reflected from the microbes and cells. A wavelength the microbes and cells absorb is detected based on the intensity of the electromagnetic wave measured by an electromagnetic wave measuring member. An electromagnetic wave absorption medium is administered to the microbes and cells so as to absorp the same wavelength of the electromagnetic wave determined by an absorption intensity distinction member while radiating the electromagnetic wave on the microbes and cells by a primary electromagnetic wave radiation member. As a result, it effectuates the functional promotion and suppression of the specified microbes and cells so as to control the functional promotion and suppression of the specified microbes.

It is to be noted that the electromagnetic wave absorption medium is to absorbe the predetermined wavelength of the electromagnetic wave. It is therefore possible to reduce the toxicity of the wave absorption medium compared to the prior art counterpart, so as to neutralize the influence on human health.

According to another aspect of the invention, an electromagnetic wave radiation member radiates, electromagnetic wave toward a microbial sample including microbes, cells and substances generated from the microbes and cells. An electromagnetic wave measuring member measures electromagnetic wave reflected from the microbial sample. A data processing member generates an output data in accordance with the electromagnetic wave measured by the electromagnetic wave measuring member.

From the reason that the output data is attained in accordance with the type and quantity of the microbial ecology in the sample, it is possible to examine the microbial ecology in the sample.

According to another aspect of the invention, an electromagnetic wave radiation member radiates electromagnetic wave on a microbial sample including microbes, cells and substances generated from the microbes and cells. An electromagnetic wave measuring member measures electromagnetic wave permeated through the microbial sample. A data processing member generates an output data in accordance with the electromagnetic wave measured by the electromagnetic wave measuring member.

The output data is thus attained in accordance with the type and quantity of the microbial ecology in the sample, it is possible to examine the microbial ecology in the sample.

According to another aspect of the invention, an electromagnetic wave radiation member radiates the electromagnetic wave on a microbial sample including microbes, cells and substances generated from the microbes and cells while radiating the electromagnetic wave on a reference blank background free from sundry microbial ecology. An electromagnetic wave measuring member measures first electromagnetic wave reflected from the microbial sample while measuring second electromagnetic wave reflected from the reference blank background. A data processing member compares said first electromagnetic wave with said second electromagnetic wave so as to generate output data based on the comparison.

Based on the output data thus attained in accordance with the type and quantity of the microbial ecology in the sample, it is possible to examine the microbial ecology in the sample.

According to another aspect of the invention, an electromagnetic wave radiation member radiates the electromagnetic wave on a microbial sample including microbes, cells and substances generated from the microbes and cells while radiating the electromagnetic wave toward a reference blank background free from sundry microbial ecology. An electromagnetic wave measuring member measures the first electromagnetic wave permeated through the microbial sample while measuring the second electromagnetic wave permeated through the reference blank background. A data processing member compares said first electromagnetic wave with said second electromagnetic wave so as to generate output data based on the comparison.

From the output data thus attained in accordance with the type and quantity of the microbial ecology in the sample, it is possible to examine the microbial ecology in the sample.

According to another aspect of the invention, the data processing member generates output data based on the intensity of the specified electromagnetic wavelength. The electromagnetic wave may have s single one or a plurality of wavelengths.

According to another aspect of the invention, output data are obtained based on an electromagnetic wave having a predetermined range of wavelength.

According to another aspect of the invention, by comparing the intensity pattern of the electromagnetic wave of the reference wavelength to other intensity pattern of the electromagnetic wave, it is possible to detect the microbial ecology with a high precision.

According to another aspect of the invention, with the use of the electromagnetic wave having the wavelengths (especially 1038 $cm^{-1}$) of approx. 1038 $cm^{-1}$, 1100 $cm^{-1}$, 1140 $cm^{-1}$, 790 $cm^{-1}$ and 1055 $cm^{-1}$ it is possible to readily detect an amount of α 1–3 bond site of glucan produced by the cariogenic microbes and/or an amount of glucan and substances engendered from glucan-related circuit imaginary possible such as cell wall, fuzzy coat, donor, receptor, acceptor, enzyme or the like which resides inside and outside the microbes, so as to effectuate the pathogenic diagnosis with an ease and rapidity.

With the use of the electromagnetic wave having the wavelengths of 1026 $cm^{-1}$, 1015 $cm^{-1}$, 992 $cm^{-1}$, 855 $cm^{-1}$, 837 $cm^{-1}$ and 820 $cm^{-1}$ it is possible to easily detect an amount of α 1–6 bond site of glucan produced by the cariogenic microbes and/or an amount of glucan and substances engendered from glucan-related circuit such as cell wall, fuzzy coat, donor, receptor, acceptor, enzyme or the like which resides inside and outside the microbes. This makes it possible to readily effectuate the pathogenic diagnosis of the dental plaque so as to observe an extent of the progress to which the cariogenicity develops from the past to the present, and thus swiftly determining a risk of the dental caries for diagnosing and treating it with a high reliability.

According to another aspect of the invention, a dental caries risk distinction member is provided to determine a dental caries risk by an intensity detected by a microbial ecology detector device.

According to another aspect of the invention, with the use of a vibration control device, it is possible to oscillate the microbial sample while controlling the oscillation. This ensures stable measurement results.

Namely, when the sample is added to a solvent while stirring it, it means to mechanically or molecularly vibrate the sample together with the solvents The measurement is effectuated in the suspended state, precipitated state and the transient state from the suspended state to the precipitated state. By observing the sample while vibrating it due to the temperature change, remarkable changes appear in the intensity of the specified wavelength of the electromagnetic wave. By measuring the frequency of the remarkable changes, it is possible to improve the measurement precision. In particular, it is possible to increase S/N ratio of the absorption intensity at the wavelength 1038 $cm^{-1}$.

According to another aspect of the invention, a dental caries risk distinction member determines the present state of a dental caries by comparing the two or more different wavelengths measured by the electromagnetic wave measuring member, it is possible to readily recognize the dental caries risk based on the sample taken from the patient's mouth.

According to another aspect of the invention, a comparator member compares and displays the intensity of the two or more different wavelengths measured by the electromagnetic wave measuring member, it is possible to readily recognize the present state of the dental caries taken as a sample from the patients on the basis of the displayed intensity of the two or more different wavelength.

BRIEF DESCRIPTION OF THE DRAWINGS

Preferred embodiments of the invention is described by way of examples with reference to the accompanying drawings wherein:

FIG. 1 is a block diagram of a microbe and cell function control device according to a first embodiment of the invention;

FIG. 4 is a block diagram of a microbial ecology detector device according to one embodiment of the invention;

DETAILED DESCRIPTION OF THE PREFERRED EMBODIMENTS OF THE INVENTION

Figure 2A:
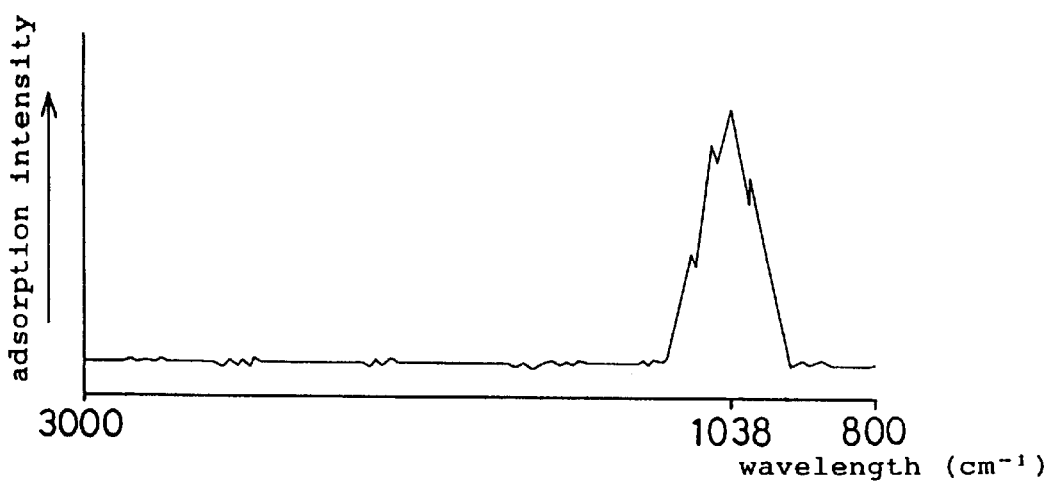
FIG. 2a is a graphical representation showing a relationship between wavelengths and electromagnetic absorption.

Referring to FIG. 1 which shows a block diagram of a microbe and cell function control device to inhibit or suppress the promotion of the pathogenic germs of the dental caries, the microbe and cell function control device 1 has a primary elctromagnetic wave radiation member 2 which radiates a predetermined wavelength range of electromagnetic wave (e.g., approx. 3000~800 $cm^{-1}$) on a dental plaque (A) taken from a tooth of a patient. An electromagnetic wave measuring member 3 is provided to measure an intensity of the electromagnetic wave within a predetermined range of the wavelengths reflected or permeated from the dental plaque (A) with the plaque (A) as a sample including germs to be detected. An absorption intensity distinction member 4 is provided to determine a peak absorption of the wavelength based on the electromagnetic wave absorption intensity measured by the electromagnetic wave measuring member 3. A secondary electromagnetic wave radiation member 5 is provided to radiate the electromagnetic wave having the wavelength determined by the absorption intensity distinction member 4 inside the patient's mouth. A display device 6 is provided to display dental clinicians the distinction data obtained from the absorption intensity distinction member 4. A main control member is provided to control the above members although not shown.

In this instance, the absorption intensity distinction member 4, the display device 6 and the main control member may be constituted by a general-purpose computer.

As a sample, the patient's plaque (A) is placed on a measurement cell (S) which has a property of permeating the electromagentic wave such as zinc celenide, zinc celnium or the like. An aqueous component reducing member (hot-air generator) is provided to reduce a aqueous component such as, for example, saliva from the plaque (A) placed on the cell (S).

The primary electromagnetic wave radiation member 2 radiates the electromagnetic wave (e.g., approx. 3000~800 $cm^{-1}$) on the plaque (A) placed on the cell (S). The primary electromagnetic wave radiation member 2 hat an infrared ray producing device 2a which emanates a wide range of the infrared ray beams, and having a wavelength selection device (band path filter) 2b which selects the electromagnetic wave having wavelength of 3000~800 $cm^{-1}$.

It is to be observed that the predetermined wavelength range of the electromagnetic wave may be continuously generated from the wavelength selection device 2b while changing the wavelength. Based on the intensity of the predetermined wavelength range of the electromagnetic wave emitted and detected by the electromagnetic wave measuring member 3, it is possible to calculate the absorption intensity of the electromagnetic wave against the sample with the use of Fourier transformation.

The electromagnetic wave measuring member 3 uses a Hydrargyrum-Cadmium-Tellurium sensor to measure an intensity of the electromagnetic wave reflected from the plaque (A).

The absorption intensity distinction member 4 is provided to specify the peak absorption of the wavelength based on the electromagnetic wave absorption intensity measured by the electromagnetic wave measuring member 3.

By way of example, as shown in FIG. 2a, the absorption intensity of the wavelength is determined based on the intensity of the electromagnetic wave measured by the electromagnetic wave measuring member 3. When a plurality of absorption peaks appear in the proximity of 1038 $cm^{-1}$, the absorption intensity distinction member 4 determines an average value of the pluralistic absorption peaks as a wavelength of the absorption peak (in the proximity of e.g., 1038 $cm^{-1}$=9.6 $\mu$m). The data processed by the absorption intensity distinction member 4 is displayed on the display device 6 for the dental clinicians in the form of absorption intensity curve against the wavelength.

The secondary electromagnetic wave radiation member 5 has a combination of the infrared-generating device and the band path filter to emanate the electromagnetic wave having the wavelength determined by the absorption intensity distinction member 4 inside the mounth of the patient from which the plaque (A) is taken as the sample. When the wavelength of the electromagnetic wave determined by the absorption intensity distinction member 4 is in the proximity of 1038 cm$^{-1}$, the electromagnetic wave (approx. 1038 cm$^{-1}$) is emanated inside the patient's mouth.

Figure 2B:
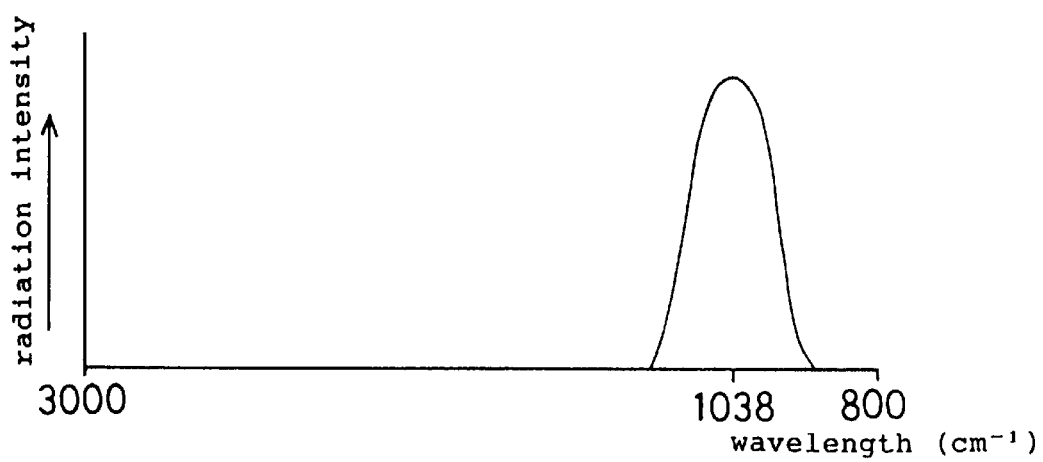
FIG. 2b is a graphical representation showing a relationship between wavelengths and electromagnetic radiation.

The germs which absorb the electromagnetic wave (approx. 1038 cm$^{-1}$) is subjected to the functional suppression. From the data attained by the experimental test results, it was found that the germs subjected to the functional suppression were cariogenic bacteria. By radiating the electromagnetic wave (approx. 1038 cm$^{-1}$ in FIG. 2$b$) inside the mouth, it is possible to suppress or control the functional promotion of the cariogenic bacteria.

In this instance, by restoring into a memory member the various absorption peaks (inputted data) which the germs represent in the patient's mouth, and comparing the inputted data with the absorbed wavelength determined by the absorption intensity distinction member 4, it is possible to emit the electromagnetic wave inside the patient's mouth only when the determined wavelength of the electromagnetic wave is the same number as the wavelength which the unnecessary germs (e.g., cariogenic bacteria) absorb in the patient's mouth.

With the use of the microbe and cell function control device 1, it is possible to quickly effectuate the functional suppression of the germs in the mouth with the specified germs as the target. This reduces the time-consuming examination routine procedures, and effectuating to suppress the dental caries appropriately depending on the patient's health condition.

When the absorption peaks of the cariogenic bacteria are known, it is possible to radiate the electromagnetic wave (e.g., 1038 cm$^{-1}$) inside the patient's mouth with the use of the single secondary electromagnetic wave radiation member 5 as a second embodiment of the invention. That is, when the absorption peaks (FIG. 3$a$) of the plaque (A) in the mouth is unknown, it is possible to emanate the electromagnetic wave (e.g., 1038 cm$^{-1}$ in FIG. 3$b$) inside the patient's mouth with the use of the secondary electromagnetic wave radiation member.

It is to be noted that a multiple wavelength light source, Fabry-Perot etalon, diffraction grating band path filter, low path filter and high path filter may be used as the wavelength selection member 2$b$. A Globar light source, ceramic light source and infrared ray lamp can be used as the electromagnetic wave source of the electromagnetic wave radiation members. When using the electromagnetic wave having the wavelength other than 1038 cm$^{-1}$, an appropriate electromagnetic wave source may be used. An interference wave may be used which is induced by interfering two or more light beams. By way of an example, when using the visible light rays and the near visible light rays, LED can be applied. With the use of laser beams, it is possible to cover a wide range from X-rays to farinfrared rays. A plurality of light sources may be selected by the correspopnding wavelength selection member to synthesize them when in use. Instead of using the plurality of light sources, the light source may be divided into a plurality of light beams. This enables to a high degree of the intensity pattern of the electromagnetic wave.

As the sensor of the electromagnetic wave measuring member 3, a quantum type photo-electromotive force sensor (Hg—Cd—Te, In—As), pyroelectric sensor (TGS), quantum type photo-conductive sensor (PbS), thermosensor (thermo-pile), thermoconductive sensor (bolometer) can be used. CCD and photodiode may be applied when using from ultraviolet rays to near infrared rays. When using the radio wave, antenna may be applied. The sensor of the electromagnetic wave measuring member 3 may preferably be in the form of array, however, it may be a single element. Upon effectuating the radiation and measurement by way of signal transmission, non-linear transfer function may be used. Otherwise, the non-linear transfer function may be rectified to be a linear function with a high precision.

As one alternative of the absorption intensity distinction member 4 differentially treats the data from the electromagnetic wave measuring member to display the peak wavelength. The member 4 further may process the peak curve with a correlative matching procedure such as FFT, wavelet, lorenz or Gauss treatment in order to isolate the peak curve so as to display it. A half value width, area or Q value of the peak curve may be calculated. A convolution and deconvolution may be used in singularity or in combination with the convergence method. The electromagnetic wave pattern obtained from the above procedure may be used to control the electromagnetic wave.

In the first embodiment of the invention, the absorption intensity distinction member 4 uses the average value. Instead of the average value, the absorption intensity distinction member 4 may use an integral calculation between wavelength sections appropriately predetermined so as to obtain the graphic representation of FIG. 2$b$ from FIG. 2$a$. A threshold value or offset may be used. Alternatively, the other band regions may be eliminated except for the absorption band region.

Figure 3A:
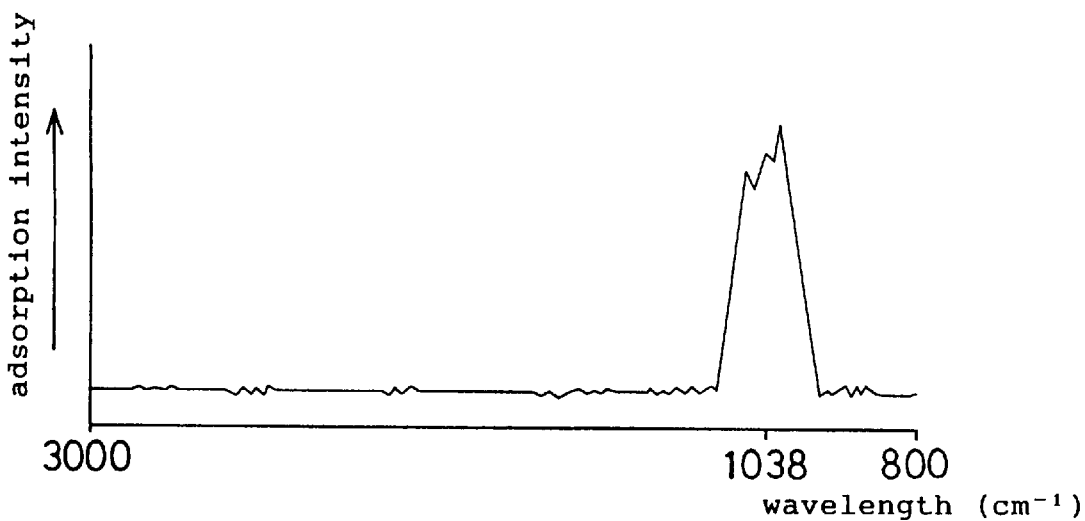
FIG. 3a is a graphical representation showing a relationship between wavelengths and electromagnetic absorption according to a second embodiment of the invention.
Figure 3B:
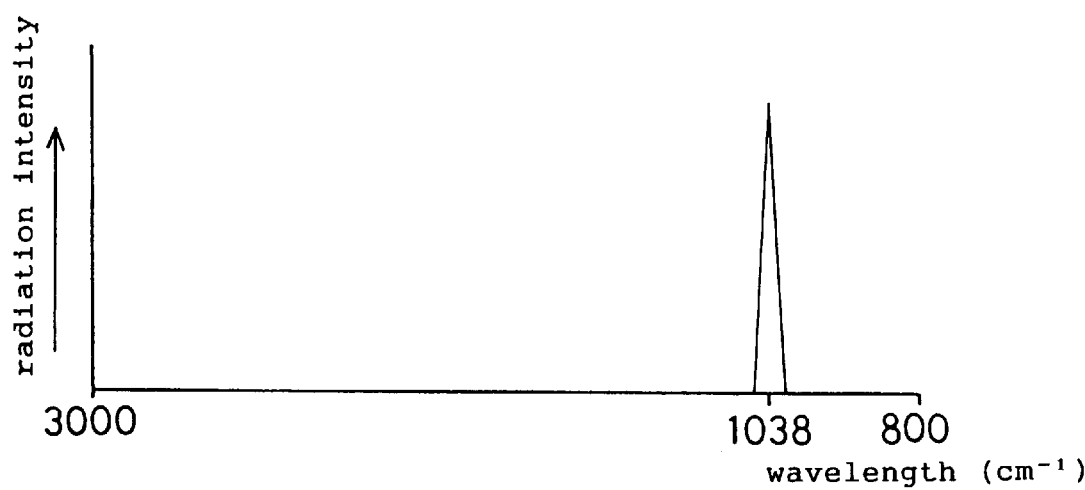
FIG. 3b is a graphical representation showing a relationship between wavelengths and electromagnetic radiation according to the second embodiment of the invention.

In the second embodiment of the invention, a single spectrum type electromagnetic wave is used as shown in FIG. 3$b$. Instead of the single spectrum, a plurality of spectra may be used. The electromagnetic wave may be radiated on each of the strains at the same time or different time. The range of the electromagnetic wave may be broadened. With the use of the peak isolation member, the graphic representation of FIG. 2$b$ (FIG. 3$b$) may be obtained from FIG. 2$a$ (FIG. 3$b$). Upon using the frequency analysis and synthesis procedures, Fourier transformation or synthesis may be incorporated into the first and second embodiments of the invention.

Instead of measuring the electromagnetic wave reflected from the sample by the electromagnetic wave measuring member 3, the member 3 may measures the electromagnetic wave permeated through the sample. Alternatively, the electromagnetic wave measuring member 3 may measure the electromagnetic wave reflected from the sample, and at the same time, measuring the wave permeated through the sample upon determining the intensity of the electromagnetic wave.

In each of the embodiments of the invention, the primary and secondary electromagnetic wave radiation members 2 and 5 may be united each other. A series of the measurement, distinction and electromagnetic wave radiation procedures may be used to form a loop. By tracing the loop repeatedly while changing the wavelength, it is possible to search, scan and converge the function of the germs.

Instead of measuring the electromagnetic wave only reflected from the microbial sample (plaque A), a reflection member (ATR crystallization) may be used to measure the electromagnetic wave reflected multiple between the microbial sample and the reflection member.

In a sample measurement portion of the microbe and cell function control device 1, an aqueous component adjusting member may be provided. The aqueous component adjusting member has at least an aqueous deprivation member which has a warm air supplying member, heating member and vacuum suction member in singularity or in combination. On the basis of the intensity data of the specified electromagnetic wave measured by the measuring member and distinction member, the aqueous component adjusting member deprives an aqueous component from the sample while giving it to the sample by means of an aqueous supplying member when necessary. Upon supplying the aqueous component, the aqueous component adjusting member is energized to open an electromagnetic valve which is connected to a water reservoir by way of a hose. A nebulizer, humidfier or atomizer may be used when the same effect is attained.

By way of illustration, the aqueous component adjusting member drives the aqueous deprivation member when the adsorption intensity at approx. 3300 $cm^{-1}$, 1632 $cm^{-1}$ and 1642 $cm^{-1}$ is more than the least value in singularity or in combination of the absorption intensity at approx. 1038 $cm^{-1}$, 1015 $cm^{-1}$, 855 $cm^{-1}$, 837 $cm^{-1}$ and 992 $cm^{-1}$.

Alternatively, a reference value or curve is prepared with the use in singularity or in combination of correlative matching procedure, recurrent curve and recurrent line in the form of primary and secondary functional curve by integrally handling the intensity curve obtained by scanning the wavelength band region from approx. 1000 $cm^{-1}$ to 800 $cm^{-1}$. When the measurement value is more than a value determined with a gradient of the reference line or curve as zero or an initial value, the aqueous component adjusting member drives the aqueous deprivation member.

Alternatively, the absorption intensity curve obtained by scanning approx. 1000 $cm^{-1}$ to 800 $cm^{-1}$ of the wavelength band region from approx. 1000 $cm^{-1}$ to 800 $cm^{-1}$ is differentially treated or calculated by a definite difference method to achieve the peak detection with the use of a calculation member. When an amplitude of the peak is nothing or appreciable, the aqueous component adjusting member drives the aqueous deprivation member.

Alternatively, the aqueous component adjusting member compares the absorption intensity at approx. 1038 $cm^{-1}$, 1015 $cm^{-1}$ or 992 $cm^{-1}$ to the absorption intensity at approx. 1632 $cm^{-1}$ and 1642 $cm^{-1}$. When the former is smaller than the latter, an aqueous deprivation signal is produced to activate the aqueous deprivation member. When the former is greater than the latter, or the former is eqaul to the latter, the generation of the aqueous deprivation signal is suspended. The absorption intensity at approx. 1038 $cm^{-1}$, 1015 $cm^{-1}$ or 992 $cm^{-1}$ may be used in singularity or in combination. These wavelengths may be used at the same time or differently divided time.

Alternatively, with the use of the peak absorption intensity at approx. 1038 $cm^{-1}$ to 1015 $cm^{-1}$, the aqueous deprivation member is activated. Then, the peak absorption intensity is compared with the absorption intensity at approx. 992 $cm^{-1}$ by using a rectangular window function. In each of the alternatives, the water supplying member may be activated when converging to the initial value. Any type of the water supplying member may be used as long as it ensures the same effect.

With the use of a sample transfer member (aluminum lamination), the sample may be taken out of the patient's mouth. With the use of the aluminum mesh or fibrinous material which does not overlap the peak absorption of the sample, it is possible to effectively absorb the aqueous component from the sample. On the other side of the sample, the aqueous component adjusting member is provided. Upon measuring the sample, a sample measurement chamber may be vacuum suctioned or may be filled with inert gas to measure it with a high precision.

In the above embodiments of the invention which exemplifies the aqueous component reducing member to eliminate the influence against the sample (plaque A), the electromagnetic wave (1500~950 $cm^{-1}$) may be radiated against the sample because of the limited influence of the aqueous component. The transfer function of the distinction member may be modified to be a rectangular function in the range of 1500~950 $cm^{-1}$. In addition, various types of signal treatments may be provided.

It is observed that the absorption intensity of the electromagnetic wave may be measured after breeding the sample for a certain period of time.

Instead of the plaque (A) taken from the human mouth, it is possible to suppress the function of the microbes (including leaven, virus) and the cells taken from human, animals, fish, birds, insects, plants and the like, which are all outside the human mouth. The technique may be utilized to activate the antagonistic bacteria beneficial to ecology in an aim to prevent certain diseases.

The wavelength is not restricted to 1038 $cm^{-1}$ characteristic of the cariogenic bacteria, the combination of the wavelengths 1038 $cm^{-1}$, 1026 $cm^{-1}$ and 1015 $cm^{-1}$ may be used to cope with the cariogenic bacteria represented by these wavelength. A resultant wave of the peak wavelengths may be used as the electromagnetic wave radiation member.

In addition to mutans streptococci (*streptococcus mutans, streptococcus sobrinus*) which involves the functional suppression of the cariogenicity (especially for suppressing the function of glucan), the technique may be used to prevent peridontal disease (porphyromonasgingivaris), actinomycosis or other diseases.

In the microbial and cell function control device 1, a vibrator device may be provided to oscillate or control the oscillation against the sample. By way of illustration, a mechanical vibrator or ultrasonic oscillator may be used. The vibration may be given to the sample depending on the temperature change. In order to enhance the sensitivity of the absorption intensity, medium wave, light rays, radio wave, magnetic and electrostatic field may be provided. In addition to the vibration control device and the temperature control device, gaseous, liquid, solid, fluid and powdered medicaments or other materials may be administered. These administering members can be used as the control and measuring means in singularity or in combination.

In place of just radiating the electromagnetic wave on the microbes and cells, and electromagnetic wave absorption medium may be used which absorbs the same wavelength as absorbed in accordance with the absorption intensity distinction member 4. The absorption medium manufactured by an absorption medium preparing member is administered to the microbes and cells so as to suppress their functions.

When the electromagnetic wave absorption peak is known to control the targetted microbes and cells, the electromagnetic wave absorption medium is prepared in correspondence to the absorption peak with the use of the absorption medium preparing member. With the use of the prepared absorption medium, it is possible to effectively control the function of the targetted microbes and cells When desired to activate the function of the cariogenic bacteria, the electromagnetic wave absorption medium can be administered which corresponds to the wavelength (approx. 1038 cm$^{-1}$).

By way of illustration, with the use of a functional substance generating member, a hydroxyapatite can be prepared to have an 9 µm wavelength absorption band region. In addition to the known hydroxyapatite generating device, a hydroxyapatite generating device is used which has a wavelength shift addition device to add a wavelength shift agent such as carbon and phosphorus. That is, with impurity additions of the carbon and phosphorus, it is possible to lengthen the absorption wavelength from 8.8 µm to 9.6 µm to prepare an electromagnetic wave absorption pellet. This widens the peak wavelength absorption band region around 9.6 µm.

Upon controlling the function of the microbes and cells, it is possible to radiate the electromagnetic wave having the absorption peak wavelength on the microbes and cells, and at same time, administering the electromagnetic wave absorption medium which absorbs the absorption peak wavelength. When controlling the function of the cariogenic bacteria, it is possible to administer the electromagnetic wave absorption medium having the absorption peak wavelength (approx. 1038 cm$^{-1}$) while radiating the electromagnetic wave having the wavelength (approx. 1038 cm$^{-1}$). The electromagnetic wave and the absorption medium may be simultaneously or discretely applied.

In lieu of the hydroxyapatite, other substances may be used as long as they are compatible with the targetted microbes in view of the absorption wavelength. In place of the phosphorus and carbon, other materials may be used. The materials may be in the form of powder, liquidity, solid, fluididity or semi-fluidity. These materials may be given by oral administration, arterial, intravenous and hypodermic injection when functionally controlling the microbes in the human body. Otherwise, these materials are used by mixing with water and paste-like substance.

With the use of the above techniques in combination, it is possible to restore the human tooth concurrently. This is because the ions of $Ca^{++}$ and $PO_4^{--}$ restores and anneals the outer surface of the tooth beside the restoring function of the hydroxyapatite. In this instance, the ions of $Ca^{++}$ and $PO_4^{---}$ may be locally administered to strengthen the restoration function. In this situation, an acid or neutralizer agent may be added to be more effective.

Upon applying the secondary electromagnetic wave radiation member, a suppression medicament may be used simultaneously to control the function of the pathogenic bacteria. By way of examples, oxides (e.g., peroxide for cariogenic bacteria), gulcan synthesis suppression media such as polyphenol, sucrose derivative, dextran-related substance, glucositase suppression agent and surface activate agent can be administered. The enzymes for the pathogenic substance (glucan) such as dextranase and mutanase may be administered. At the time of the administration, passive or active immunological substances may be added. Accompanying these pathogenic resistant factors is effective when compared to discretely using the pathogenic resistant factors alone. Antagonistic substances against the pathogenic bacteria can be accumulated. This means that the peroxide is administered to resist against *streptococcus sanguis* and *streptococcus mitis*. In this instance, a mechanically or chemically cleansing tool such as a tooth brush may be used. A radiation outlet may be attached to the tooth brush or in-between teeth brush. The electromagnetic wave radiation may be effective when using a wave guide conduit (e.g., optical fiber tube). Antibiotics, bacteria resistant medium, bactericide, protein coagulant medium as a bacteria suppression agent and ultraviolet rays as a bactericide medium can be used. A locally cooling procedure may be used to control optimal temperatures outside the range in which the pathogenic bacteria can proliferate.

In the above embodiments of the invention, the effect of the radiation and the administraion is confirmed by the functional control and emergence. An electromagnetic wave receiving member may be installed to confirm the effect by monitoring the absorption wavelength radiation corresponding to the specified function. In this instance, the radiation pattern may be divided into pulses, and the number and intervals of the pulses are adjusted to advantageously confirm the effect. With the use of this type of monitoring device, it is possible to survey the effect under the presence of a shielding member such as biosubstance. It enables to confirm the effect by fault-like distribution or indepth observation. Upon devising the electromagnetic wave receiving member, the electromagnetic wave measuring member or an absorption wavelength detection and analysis member can be used.

The electromagnetic wave can be directly or indirectly radiated based on a curve of the cariogenic microbes depending on varietal bacteria, strains of germs or serotypes each stored in the database. The electromagnetic wave radiation may be conducted by comparing or interrelating the peak wavelengths, fluctuation of the curve due to metabolic changes and data based on the peak shifts. As one example, by comparing the detected pattern data with the peak curare pattern database of the cariogenic microbe and the cariogenic related microbes (*streptococcus mutans, streptococcus sobrinus, streptococcus sanguis* and *streptococcus mitis*). The ratio of the former to the latter is determined to selectively deliver the electromagnetic wave on the sample. The radiation measurement may be conducted while measuring the electromagnetic wave radiation. This makes it possible to radiate the electromagnetic wave with a highest efficiency even when the shift occurs in the wavelengths. The range of the electromagnetic wave radiation may be broadened in a direction in which the wavelength is likely to shift. A prediction function may be stored into ROM to adjust the wavelength, the intensity and intensity pattern of the electromagnetic wave. The wavelength range of the electromagnetic wave at the absorption intensity includes approx. 790 cm$^{-1}$ and 820 cm$^{-1}$. The wavelengths of the electromagnetic wave radiated may have as follows:

1794, 1786, 1770, 1760, 1757, 1744, 1732, 1724, 1713, 1711, 1697, 1670, 1680, 1670, 1658, 1451, 1641, 1646, 1636, 1631, 1628, 1606, 1591, 1587, 1576, 1564, 1554, 1549, 1543, 1537, 1525, 1512, 1508, 1489, 1481, 1471, 1464, 1456, 1450, 1443, 1437, 1427, 1417, 1410, 1398, 1386, 1381, 1373, 1361, 1354, 1338, 1331, 1315, 1307, 1287, 1280, 1277, 1253, 1244, 1240, 1228, 1223, 1217, 1213, 1194, 1182, 1128, 1149, 1143, 1140, 1126, 1113, 1111, 1103, 1100, 1080, 1093, 1082, 1064, 1055, 1041, 1026, 1015, 999, 995, 992, 980, 968, 954, 933, 929, 924, 914, 902, 897, 883, 879, 860, 855, 837, 825, 820, 815, 810, 790 cm$^{-1}$.

Considering that the shift occurs in the wavelength depending on the substance to be radiated when the metabolism of the cariogenic microbes is renewed or suppressed, the electromagnetic wave radiation is controllably traced with the use of a shift distinction member. By screening the above wavelength absorption range with the asisst of the shift distinction member in view of the effect which is brought by each of the embodiments of the invention, it is possible to confirm the function which controls the microbial ecology so as to radiate the electromagnetic wave.

Based on the above data, it is possible for a risk distinction member to calculate, determine and display a cariogenic risk so as to appropriately adjust the intensity of the electromagnetic wave radiation.

In lieu of the infrared rays, ultraviolet rays, visible light rays and radio wave may be used. This is because the wavelength range used herein which wavelength band region is to be used may depend on the receptor, donor, acceptor, biochemical reaction cycles, enzyme and chemically bonded portion which rules the microbial function. Considering that which function is to be controlled or monitored depends on the desire of the dental clinicians, the wavelength of the electromagnetic wave to be radiated may be selected as desired. Depending on the functions to be controlled, the wavelength may be selected in singularity as well as in combination. An enire wavelength range may be used without employing a selection member.

The electromagnetic wave may be amplitude, phase or frequency modulated. The amplitude modulated waveform obtained by the modulated waves 0 Hz~100 Hz may be effective particularly in the range of 1 Hz, 15 Hz, 16 Hz, 20 Hz, 0.5 Hz~30 Hz, 40 Hz, 60 Hz, 72 Hz and 100 Hz. These frequency range may be used in singularity as well as in combination. The radiation wavelength form may be selected as desired such as sine curve, pulse, burst curve. With the use of the waveform selecting member, a plurality of waves are synthesized by means of Fourier transformation. The 0 Hz is equivalant to being in the state of electrostatic and electromagnetic field.

The electromagnetic wave may be radiated by way of a byproduct generated from the microbial metabolism. Take the cariogenic bacteria, for example, the radiation may be focused on the absorption band region of α 1–3, α 1–6 bond sites of the glucan including the glucan-related substances.

Instead of assuming the absorption spectra as indices, a light emitting spectrum and non-absorption wavelength may be selected in singularity or in appropriate combination by the distinction member and the wavelength selection member upon radiating and measuring the electromagnetic wave. Then, the electromagnetic wave is scanned to search electromagnetic wave band region and the peak wavelength to attain the same effect as using the absorption spectra.

It is to be observed that other wavelength may be used than around 9.6 μm when radiating the secondary electromagnetic wave. The wavelength band region may be a half value width (224 nm) or may be from a narrow band region (a single wavelength e.g., laser beams) to aprox. 9~10 μm band region or a wider band region. The coherent of non-coherent light wave may be used. The wavelength and the wavelength region of the light source may be variously selected. When in use, the medium wave or non-medium wave may be available depending on the purpose.

Upon selecting the specified wavelength of the light source used for the measurement and control, the electromagnetic wave may be selected with the use of the diffraction grating or filter. The multiple spectra light may be used to analyse the wave.

The filter is used to determine its permeable band region characteristics of the half value width under the variation of the individuality of the cariogenic microbe, the filter however may be changed appropriately to detect the absorption intensity in the proximity of the targetted wavelength. The window function having the Lorenz, Gauss, rectangular or triangular waveform can be used as the band path filter. Upon preparing the wavelength selection member, the N dB/oct filter (N: real number) of the at least one low path filter and high path filter may be used in individuality or in appropriate combination. The wavelength selection member may be used when operating the secondary electromagnetic wave radiation member or during the period when the singnals are processed. Additionally, the wavelength selection member may be used combinationally between the period during which the singnals are processed and the period during which the secondary electromagnetic wave radiation member is operated.

The signals detected by the measuring membermay be processed with a multiple value (e.g., two-value), added mean value, filtering, FFT, correlative or wavelet treatment.

Upon activating the primary and secondary electromagnetic wave radiation members to radiate the electromagnetic wave having a plurality of wavelengths, the wavelength pattern selection member may be arranged in parallel or series each other. When selecting the parallel arrangement, the radiation may be carried out at the same time or appropriately divided time.

A few sheets of the narrow band region filters may be incorporated into the wavelength pattern selection member. Instead of the wavelength pattern selection member, a frequency analysis member may be provided to analyse the wavelengths with the use of the multiple spectra light source.

Upon measuring the electromagnetic wave, the microbe alone, bacteria-generated byproduct, or both may be targeted. Based on the absorption wavelengths, the distinction member may select the wavelength to radiate the electromagnetic wave. The electromagnetic wave may be radiated on the sample in vivo or in vitro.

The primary electromagnetic wave radiation member and the distinction member may detect and/or analyse the electromagnetic wave. Especially when applying Fourier transformation, the transformation method is effective in specifying the electromagnetic wave. It may be necessary to rectify the sensitivity when analysing the electromagnetic wave. When using a single wavelength, only the detection member is required. When using the wavelength determined by the biochemically analysed, only an electromagnetic wave analyser may be required. Any combination of these members can be available.

Upon using the primary electromagnetic wave radiation member, the distinction member and the wavelength selection member, a microbial ecology detector device, a cariogenicity test or a cariogenicity test device may be employed.

Based on the races, ethinicity, biosphere, steadily standing microbial sphere, microbes and microbial colony, the distinction member may analyse the wavelength to obtain a representative value, mean value, central value, median, derivation value, maximum value and minimum value. The wavelength selection member may select the obtained values to feed it to each of the radiation members so as to store into a record medium such as ROM and hard disk.

In the above embodiments of the invention, the electromagnetic wave measuring member, the primary electromagnetic wave radiation member, the distinction member and the wavelength selection member may be located in singularity or in combination discretely from the secondary electromagnetic wave radiation member. With the use of an intensity determining member such as a preparation time determining member and a design time determining member, only the secondary electromagnetic wave radiation member may be installed on a dental clinic by remotely placing a wavelength absorption detector, analyser and wavelength selection member.

As one example of the above modifications, a plurality of wavelength absorption detectors and analysers may be placed to measure a plurality of microbial spheres to synthesize, equalize or statistically treat the corresponding pathogenic control wavelengths to feed to at least one of the radiation members. A representative microbes may be detected, measured and analysed respectively to obtain a representative value by the electromagnetic wave measuring member and the distinction member. The representative value, thus obtained, may be fed to each of the radiation members. Each of the members may be placed remotely and accessed by means of internet, flopy disc or other record medium.

The wavelengths indicated above are by way of examples only, and other wavelengths (including light rays) may be used as desired. By combining the first and second embodiments of the invention, it is possible to detect wavelength chracteristic of a plurality of microbial strains with the single microbial and cell function control device 1. The procedures, thus described, may be applied not only to the carirogenic bacteria but also other varietal strains of the microbes.

FIG. 4 shows a block diagram of a reflexive type microbial ecology detector device 11 which measures an amount of an α 1–3 bond site of the glucan including the glucan-related sustances, for example, the byproduct of the cariogenic microbes contained in the plague (Ao). The microbial ecology detector device 11 has an electromagnetic wave radiation member 12 which radiates the electromagnetic wave on a microbial sample (e.g., plaque Ao) taken from inside the human mouth. The plaque (Ao) contains the target microbial ecology precipitated in a cell (So). An electromagnetic wave measuring member 13 is provided to measure the electromagnetic wave reflected from the sample. A data processing member 14 is provided to generate output data in correspondence to the electromagnetic wave measured by the electromagnetic wave measuring member 13. A display device 15 is provided to exhibit the output data produced by the data processing member 14. These members are controlled by a main control member although not shown.

The plaque (Ao) is kept within the transparent cell (So) dissolved by solvent (Yo) such as, for example, water. The solution is oscillated to precipitate the plague (Ao) on which the electromagnetic wave is radiated.

The electromagnetic wave radiation member 12 is to emanate the electromagnetic wave on the plaque (Ao) placed in the cell (So). On the the plaque (Ao), radiated is the electromagnetic wave having the wavelengths of 1038 $cm^{-1}$ and 3300 $cm^{-1}$. The former is enamated to detect the amount of the α 1–3 bond site of the glucan including the glucan-related substances in the cariogenic microbes, and the latter is to measure a peak absorption wavelength of the water to use it as a reference value.

The electromagnetic wave radiation member 12 further has an infrared generator device 12a and a wavelength selection device (band path filter) 12b which permeates the specified electromagnetic wave emanated from the infrared generator device 12a.

The two types of the electromagnetic wave may be emanated in turn from the wavelength selection device 12b. Otherwise, the electromagnetic wave including the two types of waves may be first emanated to search reflected peak intensity around the two types of wavelengths based on the intensity of the electromagnetic wave detected by the electromagnetic wave measuring member 13 with the use of Fourier transformation.

The electromagnetic wave measuring member 13 uses e.g., an Hg—Cd—Te sensor to measure an intensity of the electromagnetic wave reflected from the plaque (Ao) precipitated on the bottom of the cell (So).

The data processing member 14 analyses the electromagnetic wave measured by the electromagnetic wave measuring member 13 to generate output data in accordance with the analysed results. A calculation member is provided to input various basal data depending on the intensity of the two types of electromagnetic wavelengths measured by the electromagnetic wave measuring member 13 while comparing the basal data with the analysed data of the intensity of the two types of electromagnetic wavelengths measured by the electromagnetic wave measuring member 13 so as to produce an output in accordance with the comparison.

By way of an example, the data processing member 14 previously stores the basal data in accordance with the difference between the intensity of the electromagnetic wave (approx. 1038 $cm^{-1}$) and the intensity of the electromagnetic wave (approx. 3300 $cm^{-1}$). The basal data are compared with the difference between the two intensities to determine the output data. When the difference between the two intensities is minimum, the output is generated that the amount of the α 1–3 bond site of the glucan (including the glucan-related substances) is zero percent. When the difference between the two intensities is maximum, the output is generated that the amount of the α 1–3 bond site of the glucan is (including the glucan-related substances) 100 percent. The output data thus treated by the data processing member 14 is exhibited the dental clinicians on a display device 15.

With the use of the microbial ecology detector device 11, it is possible to quickly measure the amount of the α 1–3 bond site of the glucan including the glucan-related substances the cariogenic microbes contained in the plaque (Ao). This makes it possible to readily obtain the cariogenicity information inside the patient's mouth. It may help the dental clinicians access the practical information to determine the diagnostic guidance and daily care for the dental patient.

Figure 5:
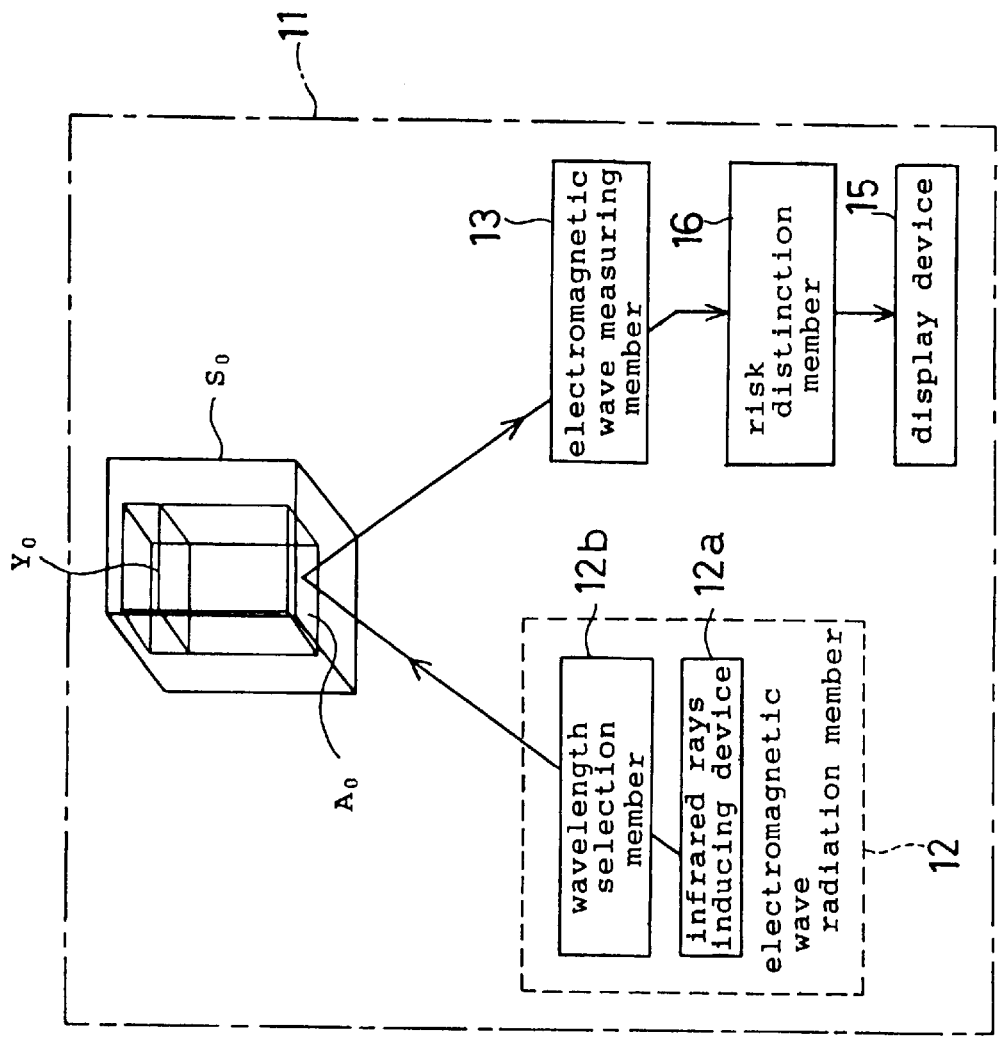
FIG. 5 is a block diagram of a microbial ecology detector device according to another embodiment of the invention.

FIG. 5 shows a block diagram of the reflexive type microbial ecology detector device 11 which measures the cariogenic condition according to another embodiment of the invention.

The microbial ecology detector device 11 has the electromagnetic wave radiation member 12 which emanates the electromagnetic wave having several (e.g., three) wavelengths on the microbial sample (plaque Ao). Instead of the data processing member 14, a cariogenic risk distinction member 16 is provided to recognize the cariogenic risk of the dental patient.

The electromagnetic wave radiation member 12 emanates the electromagnetic wave (approx. 1015 $cm^{-1}$, 855 $cm^{-1}$ and 837 $cm^{-1}$, on the plaque (Ao) placed in the cell (So) so as to measure the amount of the three varietal strains of the cariogenic microbes. In this instance, the aqueous component has been previously taken out of the plaque (Ao).

The cariogenic risk distinction member 16 regards the peak intensities of the electromagnetic waves having the wavelength of aprox. 1015 $cm^{-1}$, 855 $cm^{-1}$ and 837 $cm^{-1}$ as degrees I1, I2 and I3 respectively.

The cariogenic risk distinction member 16 compares the degrees I1, I2 and I3 to generate the output data in accordane with the comparison.

When the cariogenic risk distinction member 16 recognizes the relationship as I1>I2>I3, it displays that the cariogenic activity is in the progress with a high cariogenic risk. When representing the relationship as I1=I2>I3, it displays that the cariogenic activity is under control although its activity had been in progress in the past. When representing the relationship as I1=I2=I3, it displays that the cariogenic activity is not recognized with a low cariogenic risk. The equal notation (=) includes an approximation. The output data from the cariogenic risk distinction member 16 is exhibited the dental clinicians on the display device 15.

As opposed to the case which is to measure the electromagnetic wave reflected once from the sample, an ATR crystallization member may be provided so that the measuring member 13 can measure the electromagnetic wave reflected multiple between the ATR crystallization member and the sample. As the detector device of the measuring member 13, a quantum type photo-electromotive force sensor (Hg—Cd—Te, In—As), pyroelectric sensor (TGS), quantum type photo-conductive sensor (PbS), thermosensor (thermo-pile), thermoconductive sensor (bolometer) can be used. CCD and photodiode may be applied when using from ultraviolet rays to near infrared rays. When using the radio wave, antenna may be applied. The sensor of the electromagnetic wave measuring member 3 may preferably be in the form of array, however, it may be a single element.

As the electromagnetic wave source of the electromagnetic wave radiation members, a Globar light source, ceramic light source and infrared ray lamp can be used. When using the electromagnetic wave having the wavelength other than the present frequency, an appropriate electromagnetic wave source may be used. By way of an example, when using the visible light rays and the near visible light rays, LED or lamp can be applied. For the radio wave, the antenna can be used. With the use of laser beams, it is possible to cover a wide range from X-rays to farinfrared rays.

Instead of measuring the electromagnetic wave reflected from the sample, the electromagnetic wave permeated through the sample may be measured.

Two or more bundles of lights can be radiated on the sample to detect the interfering waves (1038 cm$^{-1}$) which reflects or permeates from the sample. With the use of two or more bundles of lights incident on the same angle, the mutual reaction of the individual wavelengths and beat frequency may be utilized. Upon processing the data based on the measurement results, the electromagnetic wave measuring member 13 may measures the electromagnetic waves both reflected and permeated from the sample as described hereinafter in FIG. 7.

Figure 6:
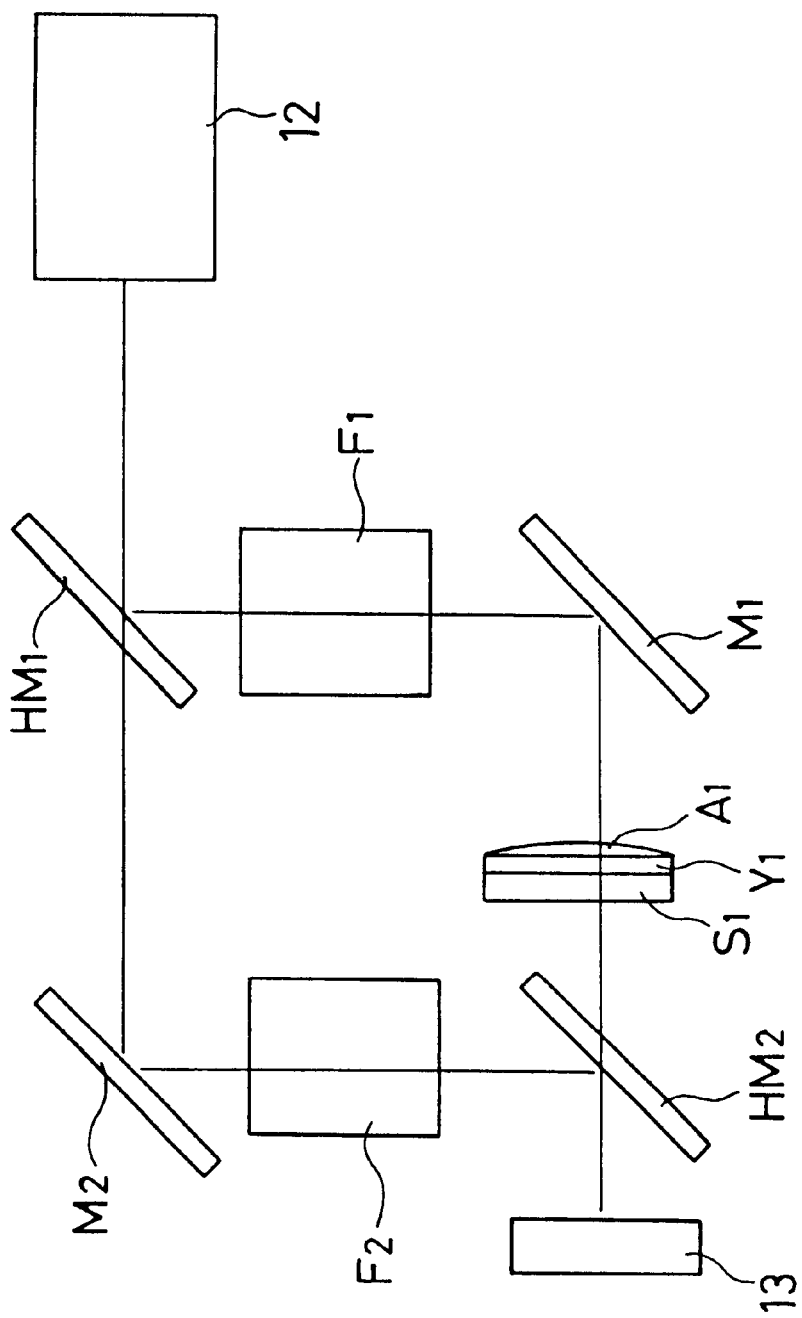
FIGS. 6 and 7 are block diagrams of measurement portions of the microbial ecology detector device according to modification forms of the preceding two embodiments of the invention.

FIG. 6 illustrates an example to measure the electromagnetic waves both reflected and permeated from the sample. In FIG. 6, Notation S1 shows a transparent sheet, Y1 a breeding medium (e.g., agar) for breeding the microbial ecology, and A1 a microbial sample. In the cell, placed is the breeding medium in which nutrients or a mixture of the substance for the specified germs is contained. On the breeding medium, Streptococcus related germs, its colony or palque (A1) is planted appropriately. Any cell will be applied as long as it can permeate the electromagnetic wave and preserve the sample. The breeding medium may be eliminated depending on the situation.

Notations HM1 and HM2 show half mirrors, M1 and M2 means mirrors and F1, F2 are frequency shifters. The electromagnetic wave emanated from the radiation member 12 introduced into two ways, one of which directs the wave to permeate the sample (A1), the breeding medium Y1 and the transparent sheet S1 so as to be measured at the intensity by the electromagnetic wave measuring member 13. At least one of the frequency shifters F1, F2 may be eliminated. The beams of the electromagnetic wave may be deformed by means of a beam magnifier tool.

With the use of the electromagnetic wave radiation member 12, it is possible to induce the coherent light wave with a high precision. The heterodyne frequency and beat wave may be used to determine the wavelengths to be 9.4, 9.6 and/or 9.8 $\mu$m by the frequency shifters F1, F2 and the electromagnetic wave measuring member 13 so as to be appropriate for observation in singularity or in combination. The laser beams can be used which enables to emit the wavelength having 9.4, 9.6, 9.8 $\mu$m and/or 1~20 $\mu$m appropriate for observation in singularity or in combination.

Figure 7:
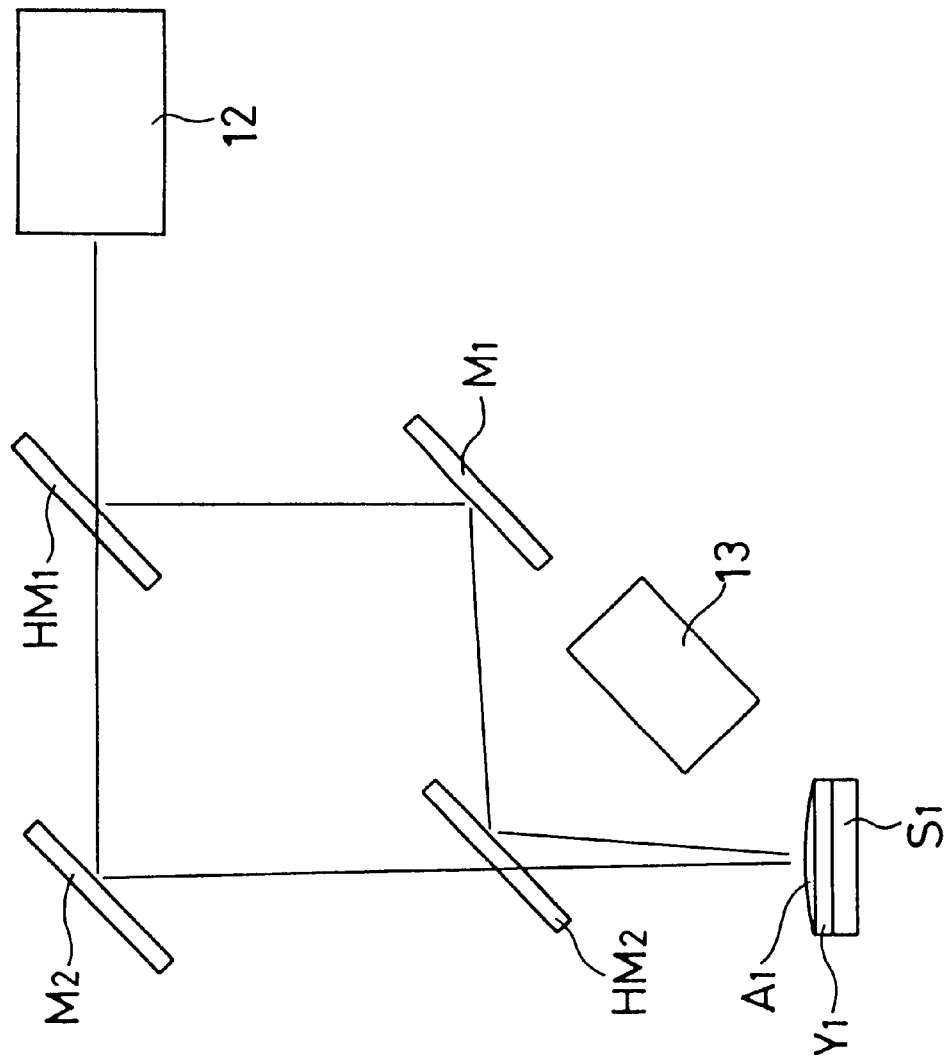

While emitting the coherent light wave by the radiation member 12, the sythesized coherent light waves may be radiated on the sample (A1). The light waves reflected or permeated from the sample may be measured by the measuring member 12 as shown in FIG. 7. The measuring member 12 may be a combination of a plurality of laser beams. By using one or more non-linear optical crystal diodes or laser beams, a plurality of wavelengths of the light waves may be induced.

As an alternative, hologram may be informed by the reflected or permeated light waves with the wave of the radiation member 12 as reference light rays. This ensures to register with a realtime observation. The materials used herein are depending on the electromagnetic wave and the dimension of the sample.

With the use of an optical circuit as shown in FIGS. 6 and 7, a test sample may be placed on one optical path, and a reference sample placed on the other optical path. The synthesized light wave may be measured.

By using only the coherent light waves detected, the cariogenic microbes can be observed at realtime as shown in FIGS. 6 and 7. The optical elements used herein are prepared in accordance with the observation wave of the electromagnetic wave source and the frequency shifters. The material used herein and coated on the mirrors, and a beam splitter are appropriately selected.

In lieu of applying the water (H$_2$O) as the reference intensity of the electromagnetic wave, a peak absorption wavelength of the liquid sucrose may be used. The reference intensity of the electromagnetic wave may be the wave reflected or permeated from the solvent (Yo) containing cell (So) without the sample. It may be the tranparent sheet (S1) and the breeding medium (Y1) in FIGS. 6 and 7.

In place of using the reference intensity of the electromagnetic wave, only the wavelength (1038 cm$^{-1}$) may be exclusively used.

The sample may be examined after breeding it in the cell (So) for a predetermined time period. Saliva may be taken out of the patient's mouth to examine the germs, microbes and their byproduct in the saliva instead of the plaque (Ao). Other germs, microbes, cells, leaven and their byproduct outside the mouth may be examined.

In the present invention, two or more types of electromagnetic waves (wave pattern) may be used to radiate the wave on the sample so as to utilize the wave reflected or permeated from the sample. With the use intensity pattern, the strains of the bacteria may be identified to enhance the measurement precision.

In another embodiment of the invention, two types of the electromagnetic waves may be used instead of three. Four or more types of the electromagnetic waves may be used with the reference intensity of the electromagnetic wave.

The cariogenicity distinction may be detected by the intensity change of the electromagnetic wave with the elapse of time.

The pluralistic intensities of the electromagnetic wave (different wavelengths) are compared to detect the cariogenicity. The data about pluralistic intensities are displayed on the displace device to provide information to help the dental clinicians judge the cariogenicity.

Upon collecting the data and judging the risk factors, it is based on the absorption intensity of the electromagnetic wave ($\alpha$ 1–3 bond site of the glucan including the glucan-related substance: 1038 cm$^{-1}$, $\alpha$ 1–6 bond site of the glucan including the glucan-related substances: 1015 cm$^{-1}$). This may be done based on the maximum intensity peak wavelength or an amount of its shift by scanning a predetermined wavelength band region.

By way of example, the data processing member 14 differentially treats the data from the electromagnetic wave measuring member to display the peak wavelength. The member 14 further may process the peak curve with a correlative matching such as FFT, wavelet, lorenz or Gauss treatment in order to isolate the peak curve so as to display it. A half value width, area or Q value of the peak curve may be calculated. A convolution and deconvolution may be used in singularity or in combination with the convergence method. The electromagnetic wave pattern obtained from the above procedures may be used to control the electromagnetic wave.

It is possible to display a characteristic curve of the cariogenic microbes depending on varietal strains of bacteria, or serotypes each stored in the database. The electromagnetic wave radiation may be emitted by comparing or interrelating the peak wavelengths and the fluctuation of the curve due to the metabolic changes and the data based on the peak shifts. As one example, this is done by comparing the detected pattern data with the peak curve pattern based on the detabase of the cariogenic microbe and the cariogenic related microbes (*streptococcus mutans, streptococcus sobrinus, streptococcus sanguis* and *streptococcus mitis*). The ratio of the former to the latter is determined to selectively deliver the electromagnetic wave on the sample.

By way of an example of the data processing member, it is judged that the cariogenic condition is highly in the progress when the absorption intensity shifts toward the shorter wavelength with a high Q value. In proportion to the dimension of the peak wavelength areas, the cariogenic risk can be judged. The risk may be judged by the product of glucan considering the glucan-related production changes under the influence of aerobic, anerobic or moderate atmosphere.

Instead of using the wavelength 1038 cm$^{-1}$ for $\alpha$ 1–3 bond site of the glucan including the glucan-related substances, the wavelength 1015 cm$^{-1}$ may be used for $\alpha$ 1–6 bond site of the glucan including the glucan-related substances. With the use of the data processing member 14, it is possible to compare the $\alpha$ 1–3 bond site of the glucan product and the $\alpha$ 1–6 bond size of the glucan-related product to calculate its ratio to display the ratio on the display device. From the data, it is possible for the risk distinction member to judge the cariogenicity depending on the amount of the $\alpha$ 1–3 bond site of the glucan-related product by way of the display device. When judging the magnitude of the cariogenicity, the wavelength 1055 cm$^{-1}$ may be used. Any wavelength will do as long as the same effect can be obtained.

As an alternative of the cariogenic distinction member, the following distinction procedures can be used.

When representing the relationship as I4<I1, I4>I2 and I4>I3, it is judged that the cariogenic condition is in the progress with a high risk.

When representing the relationship as I4<I1, I4<I2 and I4≧I3, it is judged that the cariogenic condition was in the progress in the past with high risk.

When representing the relationship as I4<I1, I4<I2 and I4<I3, it is judged that the cariogenic condition is under control with a low risk.

The comination of I1, I4 and I3, I4 may be used. I3 means the absorption intensity at the wavelength 992 cm$^{-1}$.

Instead of comparing the difference, an addition, deduction multiplication method can be used. Any method will do as long as the same effect can be obtained.

Upon using the risk distinction member, the cariogenic risk may be displayed when the Q value is high at the wavelengths 1000~1100 cm$^{-1}$, 1055 cm$^{-1}$, 1038 cm$^{-1}$ and 1015 cm$^{-1}$. It holds ture when the larger area or narrow half value width is obtained.

Considering the case in which the wave adsorption range of the $\alpha$ 1–3 and $\alpha$ 1–6 bond sites of the glucan-related product varies, it is possible to provide a registering media (RO) to rectify the variation by means of an index absorption intensity pattern, In the case of the *Streptococcus mutans* of pure strain, it repressents the wavelengths 1020~1014 cm$^{-1}$. The variation may be stored into ROM as a prediction function since the wavelength range varies depending on the breeding conditions.

Considering that the shift involves the absorption peak intensity of an entry of foreign matters, it is possible to isolate the peak wavelength from an optimum curve to enhance the measurement precision.

Instead of using the detector device of the measurement member which has high sensitivity at longer wavelengths, a sensitivity is rectified to attain a flat section at the characteristic curve. The peak wavelength of the rectified sensitivity tends to shift toward shorter wavelengths. The shift may be amended by rectifying the sensitivity and the wavelength with the use of ROM.

The wavelength range of the electromagnetic wave at the absorption intensity includes approx. 790 cm$^{-1}$ and 820 cm$^{-1}$. The wavelengths of the electromagnetic wave radiated may have as follows:

1794, 1786, 1770, 1760, 1757, 1744, 1732, 1724, 1713, 1711, 1697, 1680, 1670, 1658, 1646, 1641, 1636, 1631, 1628, 1606, 1591, 1587, 1576, 1564, 1554, 1549, 1543, 1537, 1525, 1512, 1508, 1489, 1481, 1471, 1464, 1456, 1451, 1450, 1443, 1437, 1427, 1417, 1410, 1398, 1386, 1381, 1373, 1361, 1354, 1338, 1331, 1315, 1307, 1287, 1280, 1277, 1253, 1244, 1240, 1228, 1223, 1217, 1213, 1194, 1182, 1149, 1149, 1128, 1126, 1113, 1111, 1103, 1093, 1082, 1080, 1064, 1041, 1026, 1026, 999, 995, 980, 968, 954, 933, 929, 924, 914, 902, 897, 883, 879, 825, 815, 810 cm$^{-1}$.

Considering that the shift occurs in the wavelength depending on the substance to be radiated when the metabolism of the cariogenic microbes is renewed or suppressed, the electromagnetic wave radiation is controllably traced with the use of a shift distinction member. Based on the shift information, it is possible to judge the cariogenic microbes by recognizing the shift when metaphmorphose glucan from glucose.

The light waves used herein may be provided by the diffrafction grating and filter. The multiple spectra may be divided by the wavelength.

The filter is used to determine its permeable band region characteristics of the half value width under the variation of the individuality of the cariogenic microbe, the filter however may be changed appropriately to detect the absorption intensity in the proximity of the targetted wavelengths. The window function having the Lorenz, Gauss, rectangular or triangular waveform can be used as the band path filter. Upon preparing the wavelength selection member, the N dB/oct filter (N: real number) of the at least one low path filter and high path filter may be used in individuality or in appropriate combination. The wavelength selection member may be used when activating the secondary electromagnetic wave radiation member or during the period when the singnals are processed. Additionally, the wavelength selection member may be used combinationally between the period during which the singnals are processed and the period during which the secondary electromagnetic wave radiation member is operated. An inner space of a sample chamber may be vacuumed or replaced by inert gas to enhance the measurement precision.

Upon radiating the electromagnetic wave of different wavelengths, the wavelength pattern selection member may be arranged in parallel or series each other. When selecting the parallel arrangement, the radiation may be carried out at the same time or appropriately divided time.

A few sheets of the narrow band region filters may be incorporated into the wavelength pattern selection member. Instead of the wavelength pattern selection member, a frequency analysis member may be provided to analyse the wavelengths with the use of the multiple spectra light source.

A reference absorption intensity detection member may be provided with the microbial ecology detector device. Instead of the reference absorption intensity detection member, the data may be used which memorizes the background to use the data when measuring the intensity of the electromagnetic wave. Signals detected by the measuring member may be processed with a multiple value (e.g., two-value), added mean value, filtering, FFT, correlative or wavelet treatment.

In the microbial ecology detector device 11, a vibrator device may be provided to oscillate or control the oscillation against the sample. By way of illustration, a mechanical vibrator or ultrasonic oscillator may be used. The vibration may be given to the sample depending on the temperature change. When the solvent (Yo) is contained in the sample, the solvent (Yo) is also exposed to the vibration.

When the sample is added to the solvent (Yo) while stirring the sample, it is possible to measure the wave at the suspended condition, the precipitated condition or the transcient time from the suspended condition to the precipitated condition. By observing the wave while supplying the convection due to the temperature change, it is possible to recognize a remarkable change in the intensity of the electromagnetic wave. The degree of the change provides a higher measurement precision.

With the use of an aqueous component adjusting member (hot-air generator, hygroscopic member), it is possible to taken out of the aqueous component from the sample.

In the microbial ecology detector device 11, the aqueous component adjusting member may be provided. The aqueous component adjusting member has at least an aqueous deprivation member which has a hot air supplying member, heating member and vacuum suction member in singularity or in combination. On the basis of the intensity data of the specified electromagnetic wave measured by the measuring member and distinction member, the aqueous component adjusting member deprives an aqueous component from the sample while giving it to the sample by means of an aqueous supplying member when necessary. Upon supplying the aqueous component, the aqueous component adjusting member is energized to open an electromagnetic valve which is connected to a water reservoir by way of a hose. A nebulizer, humidfier or atomizer may be used when the same effect is attained.

By way of illustration, the aqueous component adjusting member drives the aqueous deprivation member when the absorption intensity at approx. 3300 $cm^{-1}$, 1632 $cm^{-1}$ and 1642 $cm^{-1}$ is more than the least value of singularity or combination of the absorption intensity at approx. 1038 $cm^{-1}$, 1015 $cm^{-1}$, 855 $cm^{-1}$, 837 $cm^{-1}$ and 992 $cm^{-1}$.

Alternatively, a reference value or curve is prepared with the use of singularity or combination of corelation matching, recurrent curve and recurrent line in the form of primary and secondary functional curve by integrally treating the intensity curve obtained by scanning the wavelength band region from approx. 1000 $cm^{-1}$ to800 $cm^{-1}$. When the measurement value is more than a value determined with a gradient of the reference line or curve as zero or an initial value, the aqueous component adjusting member drives the aqueous deprivation member.

Alternatively, the absorption intensity curve obtained by scanning approx. 1000 $cm^{-1}$ to 800 $cm^{-1}$ of the wavelength band region from approx. 1000 $cm^{-1}$ to 800 $cm^{-1}$ is differentially treated or calculated by a definite difference method to achieve the peak detection with the use of a calculation member. When an amplitude of the peak is nothing or appreciable, the aqueous component adjusting member drives the aqueous deprivation member.

Alternatively, the aqueous component adjusting member compares the absorption intensity at approx. 1038 $cm^{-1}$, 1015 $cm^{-1}$ and/or 992 $cm^{-1}$ to the absorption intensity at approx. 1632 $cm^{-1}$ and/or 1642 $cm^{-1}$. When the former is smaller than the latter, an aqueous deprivation signal is produced to activate the aqueous deprivation member. When the former is greater than the latter, or the former is eqaul to the latter, the generation of the aqueous deprivation signal is suspended. The absorption intensity at approx. 1038 $cm^{-1}$, 1015 $cm^{-1}$ or 992 $cm^{-1}$ may be used in singularity or in combination. These wavelengths may be used at the same time or differently divided time.

Alternatively, with the use of the peak absorption intensity at approx. 1038 $cm^{-1}$ to 1015 $cm^{-1}$, the aqueous deprivation member is activated. Then, the peak absorption intensity is compared with the absorption intensity at approx. 992 $cm^{-1}$ by using a rectangular window function. In each of the alternatives, the water supplying member may be activated when converging to the initial value when regarding the peak of ($H_2O$) as the reference. Any type of the water supplying member may be used as long as it ensures the same effect.

With the use of a sample transfer member (aluminum lamination), the sample may be taken out of the patient's mouth. With the use of the aluminum mesh or fibrinous material which does not overlap the peak absorption of the sample, it is possible to effectively absorb the aqeous component from the sample.

The vibration may be given to the sample or sample molecules depending on the temperature change. In order to enhance the sensitivity of the absorption intensity, medium wave, light rays, radio wave, magnetic and electrostatic field may be provided. In addition to the vibration control device and the temperature control device, gaseous, liquid, solid, fluid and powdered medicaments or other materials may be administered. These administering members can be used as the control and measuring means in singularity or in combination.

The cariogenic sugar (e.g., sucrose) may be added to the water solution and breeding medium to stay for observation. This makes it possible to judge the risk against the cariogenicity. By adding other ingesitive foods and observing vicissitudes of the cariogenicity, it is possible for the dental clinicians to help direct the dietary practice to the dental patient.

The cariogenic microbes (hydroxyapatite) or preferential agent of its influential microbes may be added to the breeding medium. In the case of the *Streptococcus mutans,* bacitracin may be added. This eliminates the influence of the sundry germs without using sterilized water. Considering that the the *Streptococcus mutans* has fondness for the hydroxyapatite as an habitat and breeding place, an entry of the hydroxyapatite activates the proliferation and metabolism of the Streptococcus.

Instead of using the unknown or half known microbial sample, known strains of microbes may be used to serve as a biochemical reaction device as represented by Nos. of IFO.

With the use of various test medicaments and ingestive foods including artificial, synthetic sweetener as nutrients to the breeding medium, it is possible to determine what types of the materials are efficacious to resist the cariogenicity by radiating thereon the electromagnetic wave of different wavelengths. This resultantly leads to identifying the relationship between the cariogenicity suppressing waves, medicaments, ingestive foods and germs.

By adding the human saliva to the ingestive foods, the cariogenicity may be examined. This makes it possible to help understand how far the cariogenicity inducing risk is influenced under the presence of the saliva. With the further use of the plaque taken out of the patient's mouth, it is possible to determine an interrelation between the saliva and the plaque. In order to put into practical use, an electromagnetic wave radiation member, a operant member (e.g., substance administering member) may be provided.

The wavelengths, intensities, intensity patterns are merely by way of example, and not confined to those thus far described in the embodiments of the invention. The preceding two embodiments of the invention may be combined to examine pluralistic strains of microbes with the single microbial ecology detector device 11.

It is to be noted that in the primary electromagnetic wave radiation member, the electromagnetic wave may be radiated through a polarized filter to detect the dependency of the microbes on the substances outside the microbes while changing the depth to be detected.

It is also to be noted that in the secondary electromagnetic wave radiation member, the electromagnetic wave may be radiated through the polarized filter to effectuate an in-depth suppression of the microbes with the least hazard on the somatic texture.

What is claimed is:

1. A method for determining a risk that a tooth of a patient contains caries comprising the steps of:
    radiating a dental plaque of a patient with electromagnetic energy to measure an amount of α 1→3 glycosidic bonds of the glucan;
    measuring the electromagnetic wave reflected from or transmitted through said dental plaque; and
    generating output data corresponding to the measured electromagnetic wave as compared to a reference wavelength.

2. The method of claim 1 wherein the wavelength of said irradiating electromagnetic wave is 1038 $cm^{-1}$.

3. The method of claim 2 wherein the reflected or transmitted electromagnetic wave is measured to determine a peak intensity of the 1038 $cm^{-1}$ electromagnetic wave, the risk of caries being determined by comparing said peak intensity with the intensity of a 3300 $cm^{-1}$ reference electromagnetic wave.

4. The method of claim 2 wherein the reflected electromagnetic wave is measured to determine an intensity of the 1038 $cm^{-1}$ wave reflected from or transmitted through said dental plaque of said patient.

5. A method for determining a risk that a tooth of a patient contains caries comprising the steps of:
    radiating a dental plaque of a patient with electromagnetic energy to measure an amount of α 1→6 glycosidic bonds of the glucan;
    measuring the electromagnetic wave reflected from or transmitted through said dental plaque; and
    generating output data corresponding to the measured electromagnetic wave as compared to a reference wavelength.

6. The method of claim 5 wherein the wavelength of said irradiating electromagnetic wave is selected from the group consisting of approximately 1026 $cm^{-1}$, 1015 $cm^{-1}$, 992 $cm^{-1}$, 855 $cm^{-1}$, 837 $cm^{-1}$ and 820 $cm^{-1}$.

7. The method of claim 6 wherein the reflected or transmitted electromagnetic wave is measured to determine an intensity of the selected 1026 $cm^{-1}$, 1015 $cm^{-1}$, 992 $cm^{-1}$, 855 $cm^{-1}$, 837 $cm^{-1}$, 820 $cm^{-1}$ or 1080 $cm^{-1}$ waves reflected from said dental plaque of said patient.

8. The method of claim 7 wherein the risk of caries is determined by comparing peak intensities of the 1026 $cm^{-1}$, 1015 $cm^{-1}$, 992 $cm^{-1}$, 855 $cm^{-1}$, 837 $cm^{-1}$, 820 $cm^{-1}$ or 1080 $cm^{-1}$ reflected or transmitted electromagnetic waves.

9. Apparatus for determining a risk that a tooth of a patient contains caries comprising:
    means for radiating a dental plaque of a patient with electromagnetic energy to measure an amount of α 1→3 glycosidic bonds of the glucan;
    means for measuring the electromagnetic wave reflected from or transmitted through said dental plaque; and
    means for generating output data corresponding to the measured electromagnetic wave as compared to a reference wavelength.

10. The apparatus of claim 9 wherein the wavelength of said irradiating electromagnetic wave is 1038 $cm^{-1}$.

11. The apparatus of claim 10, wherein the reflected or transmitted electromagnetic wave is measured to determine a peak intensity of the 1038 $cm^{-1}$ electromagnetic wave, the risk of caries being determined by comparing said peak intensity with the intensity of a 3300 $cm^{-1}$ reference electromagnetic wave.

12. The apparatus of claim 10 wherein the reflected electromagnetic wave is measured to determine an intensity of the 1038 $cm^{-1}$ wave reflected from or transmitted through said dental plaque of said patient.

13. Apparatus for determining a risk that a tooth of a patient contains caries comprising:
    means for a radiating dental plaque of a patient with electromagnetic energy to measure an amount of α 1→6 glycosidic bonds of the glucan;
    means for measuring the electromagnetic wave reflected from or transmitted through said dental plaque; and means for generating output data corresponding to the measured electromagnetic wave as compared to a reference wavelength.

14. The apparatus of claim 13 wherein the wavelength of said irradiating electromagnetic wave is selected from the group consisting of approximately 1026 cm$^{-1}$, 1015 cm$^{-1}$, 992 cm$^{-1}$, 855 cm$^{-1}$, 837 cm$^{-1}$ and 820 cm$^{-1}$.

15. The apparatus of claim 14 wherein the reflected or transmitted electromagnetic wave is measured to determine an intensity of the 1026 cm$^{-1}$, 1015 cm$^{-1}$, 992 cm$^{-1}$, 855 cm$^{-1}$, 837 cm$^{-1}$, 820 cm$^{-1}$ or 1080 cm$^{-1}$ waves reflected from said dental plaque of said patient.

16. The apparatus of claim 15 wherein the risk of caries is determined by comparing peak intensities of the 1026 cm$^{-1}$, 1015 cm$^{-1}$, 992 cm$^{-1}$, 855 cm$^{-1}$, 837 cm$^{-1}$, 820 cm$^{-1}$ or 1080 cm$^{-1}$ reflected or transmitted electromagnetic waves.

* * * * *